United States Patent [19]

Quadro et al.

[11] Patent Number: 4,826,856
[45] Date of Patent: May 2, 1989

[54] CALCIUM ANTAGONISTIC DIHYDROPYRIDINE DERIVATIVE

[75] Inventors: Giuseppe Quadro, Milan, Italy; Jean Cahn, Montrouge, France

[73] Assignees: Yason s.r.l., Milan, Italy; Sir International SA, Montrouge, France; Henning Berlin GmbH, Berlin, Fed. Rep. of Germany

[21] Appl. No.: 157,487

[22] Filed: Feb. 18, 1988

Related U.S. Application Data

[63] Continuation of Ser. No. 914,470, Oct. 2, 1986, abandoned.

[30] Foreign Application Priority Data

Oct. 4, 1985 [IT] Italy .................... 22364 A/85

[51] Int. Cl.$^4$ .................. A61K 31/445; C07D 401/12
[52] U.S. Cl. ..................................... 514/318; 546/194
[58] Field of Search ......................... 546/194; 514/318

[56] References Cited

U.S. PATENT DOCUMENTS 4,031,104  6/1977  Bossert et al. .................. 546/321 X
4,404,378  9/1983  Miyano et al. .................. 546/194 X Primary Examiner—Richard A. Schwartz
Attorney, Agent, or Firm—Bucknam and Archer

[57] ABSTRACT

The compound I

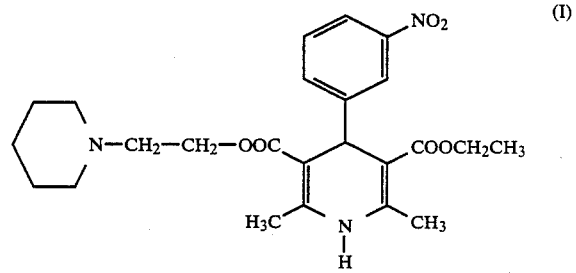

prepared by reacting m-nitrobenzaldehyde, ethyl β-aminocrotonate and 2-piperidinoethanol acetoacetate, is endowed with valuable pharmacological properties namely calcium antagonistic activity in vitro and in vivo.

5 Claims, No Drawings

CALCIUM ANTAGONISTIC DIHYDROPYRIDINE DERIVATIVE

This is a continuation of application Ser. No. 914,470, filed Oct. 2, 1986, now abandoned.

The present invention concerns a dihydropyridine derivative of formula I

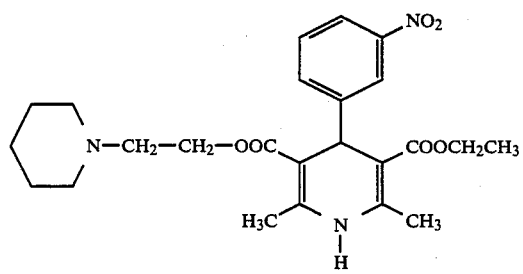

and pharmaceutically acceptable salts thereof with organic or inorganic acids, a process for its preparation and pharmaceutical compositions containing it.

Compound I or ethyl-($\beta$-piperidinoethyl)-2,6-dimethyl-4-(3-nitrophenyl)-1,4-dihydropyridine-3,5-dicarboxylate, hereinafter also named, for the sake of shortness, with the abbreviation of YS 201, possesses calcium-antagonistic activity in vitro and in vivo and it is therefore useful in human therapy.

Dihydropyridine compounds exhibiting calcium antagonistic activity have been already described and used in therapy as antihypertensive, anti-ischemic and antiarrhythmic drugs: in particular the compounds named nifedipine (U.S. Pat. No. 3,485,847 and U.S. Pat. No. 3,644,627), nicardipine (Japan Kokai No. 74 109384), nimodipine and nitrendipine (DE 2,117,571 and 2,117,583) are widely known and used.

All these compounds share a common 1,4-dihydro-2,6-dimethyl-4-(3-nitrophenyl)-3,5-pyridinecarboxylic structure and differ only in the esterification of the carboxy groups in positions 3 and 5. Nifedipine is a dimethyl ester while nimodipine, nitrendipine and nicardipine are asymmetric esters: nitrendipine is an isopropyl 2-methoxyethyl ester, nitrendipine is a methyl ethylester and nicardipine is a methyl (N-benzyl-N-methylamino)ethyl ester. Only nicardipine is characterized by the presence of an aminoester group.

A difference in the esterification results therefore in compounds having different biological characteristics and profiles. As a consequence, many research efforts have been devoted to the synthesis of various 1,4-dihydropyridine-3,5-dicarboxylic acid esters.

The introduction of a basic group into one of the two ester residues of dihydropyridinic derivatives has been described for the first time by Bayer in DE 2,218,644 (corresponding to GB 1,363,625 and U.S. Pat. No. 3,905,970). Even if compound YS 201, object of the invention, is generically comprised within the meaning of the general formula claimed in said patents, no compound having a pyperidinic group in the ester residues has been actually prepared. On the contrary, many compounds having a morpholine or a N-methylpiperazine group have been prepared.

Jap. Kokai No. 74 109384 also concerns aminoesters (nicardipine) and discloses, inter alia, only an example of a cyclic aminoester group ($\beta$-pyrrolidinoethyl).

As already mentioned, the preferred compound, which is now clinically used, is however a non-cyclic ester, i.e. nicardipine.

Other examples of dihydropyridine dicarboxylic acid basic esters are disclosed in EP-A-97821, wherein N-substituted piperazinoalkyl residues are claimed, and in EP-A-63365 wherein basic esters are claimed containing N-substituted piperidine rings and having a completely different structure than that of the compounds of the present invention.

YS 201 turned out to be surprisingly endowed with advantageous properties and with a completely different pharmacological profile with respect to the prior-art compounds.

The compound I, in particular, represents a therapeutic progress due to its activities as calcium-antagonist and as calcium-overload blocker as well as to its various mechanisms of action, which are the basis of the therapeutic efficacy of the drug in cases where the reference compounds are not so effective. This is of a particular importance in the field of cardiovascular pathology which justifies the necessity to use new compounds sometimes more selective or more effective and less toxic.

The compound YS 201 was pharmacologically compared to nifedipine, nimodipine, nitrendipine and to nicardipine, representing four structurally related and very well known dihydropyridine compounds which are presently used in human therapy, the latter being the most active aminoester compound and the only one actually entered into clinical practice. YS 201 has been also compared to two other known calcium-antagonist drugs, verapamil and diltiazem.

Acute Toxicity

The acute toxicity of YS 201 given by intraveous route, similar in the males and in the females in the rat as well as in the mouse, is as follows:

|  | in the rat | in the mouse |
| --- | --- | --- |
| LD 50: | 12.53 mg/kg | 12.29 mg/kg |
| Lower limit: | 11.65 mg/kg | 11.46 mg/kg |
| Upper limit: | 13.47 mg/kg | 13.18 mg/kg |

The acute toxicity of YS 201 given by oral route, similar in the males and in the females in the rat as well as in the mouse, is as follows:

|  | in the rat | in the mouse |
| --- | --- | --- |
| LD 50: | 402.12 mg/kg | 282.77 mg/kg |
| Lower limit: | 352.58 mg/kg | 257.55 mg/kg |
| Upper limit: | 458.62 mg/kg | 310.46 mg/kg |

Pharmacological properties

1. Inhibition of the contractile response of arterial vessels in vitro

The results of the tests hereinunder described are reported in Table 1.

1.1. Rat thoracic aorta

Aortic strips (3 mm wide) were dissected from rat thoracic aorta and bathed in a Krebs-Henseleit solution bubbled with $O_2:CO_2$ (95:5) at 38° C., under a tension of 2 g. After a 30-minutes stabilization period, a contraction was induced by adding either KCl (118 mM) or noradrenaline ($10^{-5}$ M.l$^{-1}$) in a calcium-free medium (Na EDTA 0.1 mM.l$^{-1}$) or noradrenaline (10$^{-5}$ M.l$^{-1}$) after readmission of calcium (CaCl$_2$ 1.25 mM.l$^{-1}$).

1.2. SHR aorta

YS 201 was tested in comparison with nifedipine for vasorelaxant activity in phenylephrine-(PE, 1 μM) contracted aorta from the spontaneously hypertensive rat (SHR). The compounds were added to the PE-contracted blood vessels in cumulatively increasing concentrations.

1.3. SHR aorta—Pretreatment study

SHR aorta were treated with either PE(1 μM) or high potassium (K$^+$, 80 mM) and the resulting contraction was allowed to sustain for 15 Minutes. After wash out and equilibration (1 hour), tissues were pretreated with a single concentration of either YS 201 or nifedipine. After a 30-minutes equilibration time, tissues were again challenged with either PE or K$^+$ and the resultant contraction compared to the initial contraction. Contractile effect was measured at 15 minutes after the addition of the agonist (PE or K$^+$).

TABLE 1
COMPARISON OF EC$_{50}$ OR IC$_{50}$ ON CONSTRUCTION OF AORTA STRIPS ON VITRO.

| | RAT AORTA EC$_{50}$ | | | SHR AORTA EC$_{50}$ | | |
|---|---|---|---|---|---|---|
| | | | | in vitro | pretreatment | |
| SERIES | K$^+$ | NA* − Ca$^{++}$ | NA* + Ca$^{++}$ | PHENYLEPH- RINE | K$^+$ | PHENYLEPH- RINE |
| YS 201 | 1.27 10$^{-8}$ | 1.01 10$^{-6}$ | 1.62 10$^{-5}$ | 3.9 10$^{-8}$ | 5.00 10$^{-10}$ | 3.8 10$^{-8}$ |
| NITREN- DIPINE | 3.89 10$^{-8}$ | 2.20 10$^{-7}$ | 10$^{-4}$ | — | — | — |
| NICAR- DIPINE | 4.01 10$^{-8}$ | 10$^{-4}$ | 4.08 10$^{-5}$ | — | — | — |
| NIFE- DIPINE | 1.76 10$^{-6}$ | 2.22 10$^{-5}$ | 9.80 10$^{-5}$ | 1.8 10$^{-9}$ | 2.00 10$^{-10}$ | 5.3 10$^{-8}$ |
| NIMO- DIPINE | 1.22 10$^{-6}$ | 10$^{-4}$ | 10$^{-4}$ | — | — | — |
| DILTIA- ZEM | 2.16 10$^{-7}$ | 2.01 10$^{-6}$ | 2.15 10$^{-5}$ | — | — | — |
| VERA- PAMIL | 4.92 10$^{-7}$ | 2.84 10$^{-6}$ | 2.45 10$^{-5}$ | — | — | — |

*NA = noradrenaline.

From the above reported results, it is evident that YS 201 is considerably more active than the reference compounds on the contractions induced by K$^+$ and by Ca$^{++}$ plus noradrenaline while nitrendipine is slightly more active than YS 201 on the contractions induced by noradrenaline in a Ca$^{++}$-free medium.

On SHR aortic strips both YS 201 and nifedipine are extremely potent inhibitors of the K$^+$-induced contractions.

In in vivo studies carried out on spontaneously hypertensive rats (SHR), YS 201 turned out to be endowed with a potent, dose dependent activity, especially when given by intraduodenal route. In renal hypertensive rats, YS 201, given twice a day s.c. for 10 days, significantly reduces the resting blood pressure reducing also the pressure increase elicited by anxiety and effort.

Comparative effect of YS 201 on 3 month old rats and 6 month old SHR-SP

YS 201 was given by intraduodenal route at 15 mg/kg in normotensive rats. The diastolic blood pressure (DBP) was significantly reduced by 3.1 KPA 5 min. after administration and the reduction was still significant 60 min. later. The systolic pressure was also significantly reduced (Table 2).

TABLE 2
EFFECT OF YS 201 (INTRADUODENAL ROUTE - 15 mg/kg) ON BP IN NORMOTENSIVE RATS

| PARA- ME- TERS | TO | TIME AFTER DOSING (MIN.) | | | | | | | |
|---|---|---|---|---|---|---|---|---|---|
| | | 1 | 2 | 5 | 10 | 15 | 30 | 60 | 120 |
| DBP$^1$ | 13.5 ± 0.55 | 13.0 ± 0.74 | 12.0 ± 0.35 | 10.4 ± 0.33* | 9.4 ± 0.19* | 9.8 ± 0.34* | 11.3 ± 0.62* | 12.4 ± 0.40* | 13.7 ± 0.87 |
| MBP$^2$ | 13.2 ± 0.50 | 14.8 ± 0.64 | 13.9 ± 0.28 | 12.7 ± 0.19* | 11.6 ± 0.15* | 11.7 ± 0.28* | 12.9 ± 0.51* | 14.0 ± 0.35* | 15.3 ± 0.90 |
| SBP$^3$ | 18.5 ± 0.47 | 18.4 ± 0.48 | 17.8 ± 0.26 | 17.2 ± 0.26 | 15.9 ± 0.19* | 15.6 ± 0.29* | 16.0 ± 0.35* | 17.3 ± 0.26* | 18.5 ± 1.06 |
| HR$^4$ | 432 ± 28.7 | 556 ± 9.8* | 556 ± 7.5* | 564 ± 7.5* | 536 ± 7.5* | 524 ± 11.7 | 496 ± 22.3 | 428 ± 24.2 | 416 ± 27.9 |

*P less than 0.05

In 6 month old SHR-SP YS 201 produced a more marked reduction in DBP than in SBP, the effect being lasting 4 hours (Table 2a).

TABLE 2a
EFFECT OF YS 201 (INTRADUODENAL ROUTE - 15 mg/kg) ON BP IN SHR-SP (6 MONTH OLD).

| TIME (MIN.) | PARAMETERS | | | | |
|---|---|---|---|---|---|
| | DBP$^1$ | MBP$^2$ | SBP$^3$ | S-D$^5$ | HR$^4$ |
| 0 | 17.5 | 20.0 | 25.0 | 7.5 | 360 |
| +1 | 17.0 | 19.3 | 24.0 | 7.0 | 360 |
| +2 | 15.0 | 17.5 | 22.5 | 7.5 | 360 |
| +5 | 16.0 | 18.7 | 24.0 | 8.0 | 360 |
| +10 | 13.5 | 16.2 | 21.5 | 8.0 | 360 |
| +15 | 13.0 | 15.7 | 21.0 | 8.0 | 360 |
| +30 | 11.0 | 13.7 | 19.0 | 8.0 | 340 |
| +60 | 10.0 | 12.0 | 17.0 | 7.0 | 300 |
| +120 | 11.5 | 13.5 | 17.5 | 6.0 | 360 |
| +180 | 8.0 | 9.8 | 13.5 | 5.5 | 400 |

TABLE 2a-continued

EFFECT OF YS 201 (INTRADUODENAL ROUTE - 15 mg/kg) ON BP IN SHR-SP (6 MONTH OLD).

| TIME (MIN.) | PARAMETERS | | | | |
|---|---|---|---|---|---|
| | DBP[1] | MBP[2] | SBP[3] | S-D[5] | HR[4] |
| +240 | 6.0 | 7.5 | 10.5 | 4.5 | 420 |

[1]Dyastolic blood pressure
[2]Mean Blood pressure
[3]Systolic blood pressure
[4]Heart rate
[5]Difference between systolic and diastolic blood pressure.

Ventricular arrhythmias after coronary artery ligation in the acute phase or during the period of re-circulation Sprague-Dawley rats were subjected to ligation of the left coronary artery according to the method of Clark et al. in J. Pharmacol. Methods 3, 357–368, 1980. The drugs were administered by gastric tube 30 minutes before the ligation. By means of a continuous electrocardiographic recording, the ventricular arrhythmias such as ectopic beats (EB), ventricular tachycardia (VT), ventricular fibrillation (VF) for 30 minutes after ligation, were recorded.

In another group of animals the ligation was removed after 5 minutes, causing thereby an increase of the arrhythmias and of the death-rate.

The data, reported in the two following Tables 3 and 4, show that YS 201 is able to reduce dramatically the arrhythmias: the therapeutic activity of YS 201 is in particular more potent than that of the reference drugs in inhibiting the arrhythmias after re-circulation.

age of rats exhibiting VT is significantly reduced at 1.5 mg/kg$^{-1}$. On re-circulation, both at 7.5 and at 15 mg/kg$^{-1}$ YS 201 lowers in a highly significant manner the early ECG disturbances following the release of the clamps. All of the parameters taken into account are diminisched and death is completely suppressed at 15 mg/kg$^{-1}$ (P=0.02).

Transient cerebral oligoemia in the rat

The method described by Borzeix in Circulation et Metabolisme du Cerveau 1, 63–79, John Libbey Eurotext Publ. (1983) has been followed, using male Sprague-Dawley rats about 10 weeks old having a bilateral carotid artery ligation for a 60 Minutes period. The animals were treated by the oral route with the tested drugs twice a day, starting one hour after the ligation and for 3 days, in scalar doses.

The last dose, at the 71$^{th}$ hour after the occlusion, preceeded by one hour the sacrifice of the animal, whose brain was subjected to the determination of the $H_2O$, $K^+$ and $Ca^{++}$ content.

Under said experimental conditions, a transient oligoemia gives rise to an evolutive cerebral disease which is characterized by an impairment of the neurologic behaviour, by deep biochemical disturbanced—especially a tremendous intracerebral accumulation of $Ca^{++}$ ions.

The curative administration of calcium entry blockers can interfere with the spontaneous evolution of this disease. The results, reported in Table 5, show that YS 201 suppresses any edematous reaction and prevents the $K^+$ efflux from the brain as well as it impedes the

TABLE 3

ARRHYTHMIAS DURING THE LIGATION PERIOD

| Groups | Doses mg/kg$^{-1}$ p.o. | N | Mean value of indices + SEM | | | VF % | Deth-rate % |
|---|---|---|---|---|---|---|---|
| | | | EBs | VT | VF | | |
| Controls | — | 15 | 67.1 ± 18.83 | 3.7 ± 1.57 | 5.3 ± 1.73 | 80 | 33.3 |
| Nifedi- | 1.0 | 5 | 70.0 ± 24.72 | 4.4 ± 2.22 | 1.1 ± 0.55 | 80 | 0 |
| pine | 1.5 | 5 | 40.5 ± 20.19 | 2.1 ± 1.75 | 1.7 ± 0.77 | 60 | 20.0 |
| Nicar- | 0.5 | 3 | 10.9 | 2.5 | 2.5 | 66.7 | 0 |
| dipine | 1.0 | 3 | 22.0 | 0.5 | 0.9 | 100 | 33.3 |
| | 2.0 | 4 | 31.9 | 0.7 | 1.2 | 75 | 25.0 |
| YS 201 | 0.75 | 4 | 42.1 ± 9.70 | 1.3 ± 0.68 | 3.8 ± 1.77 | 60 | 20 |
| | 1.50 | 10 | 45.7 ± 6.18 | 1.9 ± 0.32 | 0.5 ± 0.49 | 20** | 0 |
| | 3.0 | 5 | 36.0 ± 9.11 | 1.6 ± 0.77 | 4.8 ± 1.41 | 100 | 80 |

N = Number of rats per group;
**$P \leq 0.05$ according to Student test or to chi square test corrected for continuity according to Yates.

TABLE 4

ARRHYTHMIAS AFTER RE-CIRCULATION

| Groups | Doses mg/kg$^{-1}$ p.o. | N | Mean value of indices + SEM | | | VF % | Deth-rate % |
|---|---|---|---|---|---|---|---|
| | | | EBs | VT | VF | | |
| Controls | — | 15 | 116.0 ± 25.70 | 6.2 ± 1.80 | 17.6 ± 4.53 | 80 | 53.3 |
| Diltiazem | 5 | 11 | 68.9 ± 32.12 | 4.2 ± 2.54 | 8.8 ± 4.64* | 45.5 | 27.3 |
| Verapamil i.v. | 0.1 | 10 | 48.0 ± 10.1 | 1.8 ± 0.53 | 6.9 ± 4.3* | 50 | 30 |
| YS 201 | 7.5 | 10 | 42.8 ± 10.08* | 2.2 ± 1.70* | 1.3 ± 0.52* | 60 | 10** |
| | 15 | 10 | 27.20 ± 5.87* | 1.2 ± 0.39* | 0.6 ± 0.33* | 50 | 0** |

N = Number of rats per group;
*$P \leq 0.05$ according to Mann-Whitney's U test;
**$P \leq 0.10$ according to the chi square test corrected for continuity by Yates.

From the above data, it turns out that, whatever the dosage given, YS 201 reduces by nearly 2 fold the index atributed to EBs and VT but it does not interfere with the duration of VF episodes; nevertheless, the percent- $Ca^{++}$ ions to accumulate into the brain, whereas nimodipine and nicardipine, the two other dihydropyridine compounds considered, fail. A good activity is exerted by verapamil and diltiazem.

TABLE 5

BIOCHEMICAL IMPAIRMENTS IN POST-OLIGOEMIC RATS

| Groups | N | mg/kg$^{-1}$ p.o. (7 ×) | Cerebral content H$_2$O percent | K$^+$ mmol · kg$^{-1}$ | Ca$^{++}$ dry weight |
|---|---|---|---|---|---|
| Controls | 51 | — | 78.6 ± 0.06 | 485.8 ± 3.99 | 4.7 ± 0.17 |
| Post-oligoemic controls + 76 h) | 36 | — | 79.4* ± 0.23 | 385.2* ± 7.24 | 21.1* ± 2.14 |
| Nimodipine | 9 | 0.5 | 79.5* ± 0.40 | 442.0 ± 22.40** | 20.1* ± 4.36 |
|  | 11 | 1.5 | 79.3 ± 0.40 | 402.0* ± 17.52 | 16.1* ± 3.42 |
| Nicardipine | 8 | 1 | 79.6* ± 0.37 | 460.0 ± 18.96** | 18.4 ± 7.04 |
|  | 4 | 3 | 79.2 ± 0.42 | 368.0* ± 19.68 | 19.4 ± 5.0 |
| YS 021 | 8 | 0.25 | 79.2 ± 0.57 | 428* ± 15.9** | 12.6* ± 3.32** |
|  | 7 | 0.50 | 78.3 ± 0.39** | 431* ± 14.9** | 11.7 ± 3.00** |
|  | 5 | 1.0 | 77.8 ± 0.47** | 428* ± 8.2** | 11.7 ± 5.53 |
|  | 8 | 3.0 | 78.8 ± 0.44 | 425* ± 13.9** | 12.6 ± 3.89** |

N = Number of rats per group;
P ≦ 0.05 according to the Student test or the Cochran test;
*versus controls;
**versus post-oligoemic controls.

Effect of YS 201 administration on the anaphylactic bronchoconstriction in actively sensitized guinea-pigs Hartley guinea pigs are actively sensitized against ovalbumin (OA) by intraperitoneal (100 mg) and subcutaneous (100 mg) injections associated each with Freund adjuvant 50 μl. Experiments are performed three weeks after the active sensitization procedure. At that time, the animals have reached a body weight of about 600–700 g. They are anesthetized with urethane (1.25 g/kg$^{-1}$ i.p.) and allow to breath spontaneously. Bronchoconstriction is measured with a Fleisch pneumotachograph and a Presograph Godart (sensitivity 5–50 cm H$_2$O) allowing to record or to calculate the following parameters:

Inspiratory volume (i.v.): ml
Expiratory volume (e.v.): ml
d(i.v.): difference of inspiratory volume with regard to resting value (prior to OA-challenge)
Respiratory minute volume (m.v.): ml/min
Respiratory frequency (r.f.): strokes/min
Transpulmonary pressure (Trans P): cm H$_2$O
Pulmonary compliance (P.C.): ml/cm H$_2$O
Pulmonary resistance (P.R.): cm H$_2$O/ml/sec.

The anaphylactic bronchoconstriction is induced by intraveous OA-challenge (5 mg/kg) of the sensitized guinea-pigs. All animals are treated with the antihystaminic mepyramine (1.0 mg/kg i.v.) 5 min. before the OA-challenge. The test compound (YS 201) or the vehicle (distilled water) are injected subcutaneously (S.C.) 15 min. prior to the OA-challenge under a volume of 2 ml/kg. All the measurements were done at +1, 2, 3, 4, 5, 10 and 15 minutes post OA-injection. The reference value "T 0" has been considered just before anaphylactic shock, i.e. 15 minutes after YS 201 has been injected. Two dosages of YS 201 have been studied; 5 and 10 mg/kg on 7 guinea-pigs each.

The results have been analyzed using a global analysis of variance considering all the 3 series (control-YS 201: 5 mg/kg and 10 mg/kg) and all the experimental times. When a statistical differences at P level ≦0.05 appears, Least Significant Difference (LSD) test was applied to position the series the ones between the others.

The results obtained show that the effect of YS 201 can be characterized at 5 mg/kg by a minor effect on lung elasticity per se. However, this limited effect on visco-elastic properties of the lung allows possibility of the compensation of the bronchoconstriction through an increase of the inspiratory and the expiratory volumes. On the opposite, at 10 mg/kg, YS 201 seems to act directly on pulmonary compliance by increasing it and by decreasing the pulmonary resistance. This effect is clear enough to be evidenced by the global analysis of variance. The fact that the inspiratory or the expiratory volumes are not increased at this dosage is the direct consequence of YS 201 effect on the dynamic compliance which then avoids a compensatory mechanism through the respiratory volume.

To summarize, the results obtained with YS 201 indicate that this compound can protect the guinea-pig against an ovalbumin-challenge inducing anaphylactic bronchoconstriction. This property was never described for any calcium antagonist of the dihydropyridine group or of the verapamil or diltiazem like structures.

Pharmacokinetics and bioavailability

YS 201 hydrochloride was intravenously and orally administered to dogs at 1 and 10 mg/kg respectively.

After intraveous dosing the decline in YS 201 concentration was typically biexponential. The mean half-life of elimination was 88 min.

After oral administration, the appearance of secondary peaks in the plasma concentration-time profiles suppose the presence of enterohepatically recycled YS 201. An extended mean apparent half-life of elimination of 148.3 min. was exhibited after oral dosing. The mean maximum concentration was found to be 284 ng/ml and the average AUC was 64873.6 ng/ml$^{-1}$ min. These results are comparable with results obtained in dogs with nicardipine at the same dose ($\overline{C}$max=220 ng/ml and $\overline{AUC}$=76600 ng/kg$^{-1}$ min.). The average apparent bioavailable fraction was 19.4%.

Bioavailability of YS 201, after oral administration in normal volunteers

The study was performed in 4 male subjects aged 26–43 years.

Pharmacokinetic studies were performed both after acute and repeated administrations.

Acute administration

Each volunteer received one capsule of 20 mg of YS 201 with a glass of water.

Further venous blood samples were withdrawn 15–30 minutes and 1.0–1.5–2.0–4.0–6.0–8.0 hours after treatment.

Multiple-doses administration

The same four volunteers, after the first administration were treated with increasing doses of YS 201: 30-4-0-50 mg.

Blood samples were withdrawn 2-4-8-12 hours after the last treatment.

Plasma levels of unchanged YS 201 were assayed with a specific HPLC method.

The pharmacokinetic parameters obtained are reported in the following Table 6.

TABLE 6

| | PHARMACOKINETICS PARAMETERS | | | | |
|---|---|---|---|---|---|
| Vol. n. | C max $\mu g/kg^{-1}$ | T max (h) | T½ el. (h) * | ** | AUC $\mu g/ml/h$ |
| 1 | 56 | 1.5 | 1.99 | 4.11 | 0.219 |
| 2 | 55 | 1.5 | 1.05 | 4.44 | 0.181 |
| 3 | 65 | 2 | 1.80 | 4.12 | 0.269 |
| 4 | 83 | 1 | 2.66 | 4.49 | 0.388 |
| Mean | 64.75 | 1.5 | 1.88 | 4.29 | 0.252 |
| ± S.D. | 12.97 | 0.40 | 0.66 | 0.10 | 0.068 |

*after acute administration;
**after multiple-doses administration.

Plasma profiles in the acute study indicate a rapid absorption of YS 201, as evidenced by the average T max of 90 min. The mean value for peak plasma level was 57.25 ng/ml±2.65 ($\bar{x}$±S.E.).

Corresponding with the phase of distribution and excretion of the drug, the plasma levels decline; the mean value for T½ el. was 1.8 hours±0.65 S.D.

After six hours the unchanged drug is still present in the plasma.

In the multiple dose study, two hours after the last treatment with increasing doses, the plasma levels of unchanged drug are three times upper, as to values dosed at the same time after acute treatment.

Four hours after administration, the plasma levels are reduced to the half, as to the peak.

Twelve hours after treatment, YS 201, as unchanged drug, is still present in the plasma.

The compartment analysis shows that the plasma profile of unchanged drug declines in one phase, both after acute and repeated administration; in the first case, however, the levels decline more rapidly, as indicated by the shorter mean terminal half life: 1.8 hours after acute administration; 4.29 hours after repeated administration.

The difference between such values could be related to the increase of the doses administered, as reported by many Authors in some other cases ("Biopharmaceutics and Relevant Pharmacokinetics"—Wagner J. G.—Drug Intelligence Pubblications, Hamilton, Ill., 1th Edition, 1971).

Clinical tolerance

The oral treatment with YS 201 was well tolerated: the normal respiratory function as well the other vital parameters were not affected.

Concerning the cardiovascular function, any pathological modification of the arterial pressure was not observed; in two subjects (n. 3, 4), however, a moderate but definite sinus bradycardia was registered.

The atrio-ventricular conduction time (PR interval) was slightly prolonged in two subjects (n. 1, 2). Such interval was delayed from 0.14 to 0.16 sec. (subject n. 1) and from 0.16 to 0.18 sec. (subject n. 2).

These modifications should be reasonably related to the calcium-antagonistic effect of YS 201 on the superior portion of the specific conduction system.

All the results obtained give evidence that YS 201 is a potent calcium-antagonist but also a calcium-overload blocker according to the definition given by van Zweiten (1985, Arzn. Forsch. I Drug Research 35 (1). Nr. Ia: 298-301). The drug can be used for the treatment of cardiac ischemic disease by blocking the increase content of calcium in the heart and therefore reducing the infarct area, for the treatment of ventricular arrhythmias and of paroxystic ventricular tachycardia, for the treatment of ectopic and premature beats and for the prevention of sudden-death by cardiac fibrillation in angina pectoris. The drug can be used also for the treatment of cerebral vasospasms and in the early treatment of stroke in order to reduce the increased accumulation of calcium resulting from brain ischemia.

The drug can also be used in the treatment of essential hypertension not only because it reduces MABP, SABP and DABP in resting conditions but also because it blocks the hypertensive response to anxiety and effort which is a characteristic of human essential hypertension.

The drug could also be used in the treatment of allergic asthma and it must be stressed that the effect on the lung and the bronchi could be obtained without influencing the cardiac work as it is observed with the phosphodiesterase-inhibitors actually used in the treatment of said disease.

The whole pharmacological profile of YS 201 turns out to be remarkably different from that of other calcium antagonists, even belonging to the dihydropyridine series.

It must be stressed that pharmacologically acceptable salts of YS 201 have substantially the same activity of the free base.

The salts obtained through the variation of the acid used in some cases have special advantage due to increased stability, increased solubility, decreased solubility, ease of crystallization, lack of objectionable taste, etc., but these are all subsidiary to the main physiological action of the free base, which is independent of the character of the acid used in the preparation of the salt.

For the therapeutic use, YS 201 or a salt thereof will be administered in form of pharmaceutical compositions suited for the oral, parenteral or transdermal compositions, formulated by using conventional carriers, excipients and methods.

Examples of said compositions include capsules, tablets, syrups, granulates, solutions, vials, etc. Particularly preferred is the use of oral, gastro-resistant and enterosoluble formulations because it has been surprisingly found that said formulations give a bioavailability much higher than that obtained by the administration of normal, non-gastro-resistant formulations.

The daily posology depend on the diagnosis and on tha patient's conditions (sex, weight, age) and generally it will range from 50 to 500 mg in 2-3 administrations.

The compound I is prepared by reacting m-nitrobenzaldehyde, ethyl β-aminocrotonate and 2-piperidinoethanol acetoacetate, according to the following scheme:

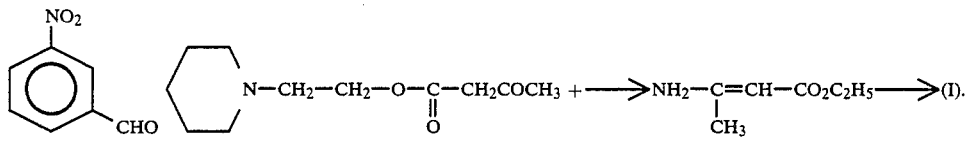

The reaction is normally carried out in the absence of solvents at a temperature of about 90°–100° C. for some hours.

m-Nitrobenzaldehyde and β-aminocrotonate are commercially available compounds or they may be prepared by known methods. 2-Piperidinoethanol acetoacetate is conveniently prepared by reaction of 1-piperidinomethanol and diketene in the presence of an amine.

The following example further illustrates the invention without limiting it in any way.

EXAMPLE (a) 2-Piperidinoethanol-acetoacetate

Diketene (8.1 ml) was added dropwise to 2-piperidinoethanol (9.36 ml) and triethylamine (0.05 ml) under stirring, so as to keep the temperature at 60°–70° C. (exothermic reaction). When the addition was over, the mixture was stirred at 80° for 40'. 12.4 g of the product were obtained by vacuum (2 mmHg) distillation. The NMR spectrum was in agreement.

(b) 12.46 g of m-nitrobenzaldehyde, 17.7 g of the product (a) and 11.8 g of β-aminocrotonate, were heated to 90° C. (exothermic reaction and gas evolution). The temperature was kept at 90°–100° C. for 6 hours. The residue was chromatographed on $SiO_2$, eluent $CH_2Cl_2$, $CH_2Cl_2$:MeOH:$Et_3N$ 95:5:0.5.

14 g of the product, melting at 185°–188° C., were obtained.

IR (mineral oil dispersion): 1680 $cm^{-1}$ ν C=O of the ester group; 2350–2700 $cm^{-1}$ ν $NH^+$ of the ammonium group.

$^1$H-$CD_3SOCD_3$): δ 1.19 (t, 3H, $CH_3$(a)), 1.69 (broad, 6H, $CH_2$(b)), 2.32 and 2.40 (s, 3H, $CH_3$(c)), 2.8–3.5 (m, 6H, $CH_2N$(d)), 4.03 (q, 2H, $CH_2$(e)), 4.45 (t, 2H, COO$\underline{CH_2}CH_2$(f)), 5.05 (s, 1H,

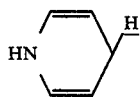

(g)), 7.5–8.1 (m, 4H, Ar), 9.45 (s, 1H, HCl).

We claim:

1. Compound of formula I

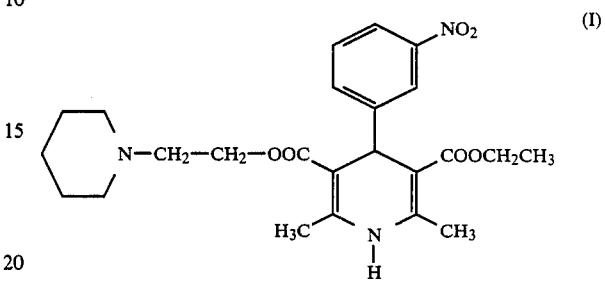

or a salt thereof with a pharmaceutically acceptable organic or inorganic acid.

2. An anti-hypertensive, anti-ischemic and anti-arrhythmic composition containing an effective amount of compound I of claim 1 or a salt thereof with at least one inert carrier and/or excipient.

3. The composition according to claim 2 in unit dose for oral, parenteral or transdermal administration.

4. A pharmaceutical composition according to claim 2 in the form of gastro-resistant and enterosoluble capsules or tablets.

5. The method of protecting a living subject from bronchoconstriction which consists of administering to said living subject in need of treatment an effective amount of the compound of formula I

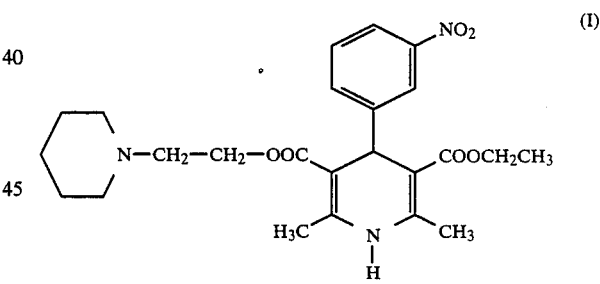

or a salt thereof with a pharmaceutically acceptable organic or inorganic acid.

* * * * *